US006638069B2

(12) United States Patent
Hagenbuch et al.

(10) Patent No.: US 6,638,069 B2
(45) Date of Patent: Oct. 28, 2003

(54) SHAPING CAP FOR DENTAL PIN STRUCTURES

(75) Inventors: Konrad Hagenbuch, Grabs (CH); Gerhard Zanghellini, Schaan (LI)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 09/933,924

(22) Filed: Aug. 21, 2001

(65) Prior Publication Data

US 2002/0025506 A1 Feb. 28, 2002

Related U.S. Application Data

(60) Provisional application No. 60/263,371, filed on Jan. 23, 2001, and provisional application No. 60/283,430, filed on Apr. 12, 2001.

(30) Foreign Application Priority Data

Jul. 12, 2000 (DE) .......................... 100 60 922
Aug. 21, 2000 (DE) .......................... 100 40 772

(51) Int. Cl.⁷ ..................... A61C 13/10; A61C 13/103; A61C 13/105
(52) U.S. Cl. ..................... 433/194; 433/191; 433/192; 433/193; 433/195; 433/201.1; 433/202.1; 433/204; 433/209; 433/210; 433/211; 433/212.1; 433/225; 264/16; 264/19; 523/113; 523/114; 523/115
(58) Field of Search ................ 433/191, 192, 433/193, 194, 201.1, 202.1, 204, 209, 210, 211, 212.1, 225, 219, 218, 220, 222.1, 195; 264/16, 19, 18, 20; 523/114, 115, 113

(56) References Cited

U.S. PATENT DOCUMENTS

| 2,237,350 | A | | 4/1941 | Hollmann | |
|---|---|---|---|---|---|
| 3,717,932 | A | * | 2/1973 | Brainin | 433/175 |
| 3,874,081 | A | * | 4/1975 | Franklin et al. | 433/225 |
| 4,199,864 | A | * | 4/1980 | Ashman | 433/175 |
| 4,224,689 | A | * | 9/1980 | Sundberg | 714/709 |
| 4,504,230 | A | * | 3/1985 | Patch | 433/219 |
| 4,678,435 | A | * | 7/1987 | Long | 433/218 |
| 4,710,127 | A | * | 12/1987 | Bellavia et al. | 433/215 |
| 5,094,620 | A | * | 3/1992 | Nordin | 433/220 |
| 5,192,207 | A | * | 3/1993 | Rosellini | 433/223 |
| 5,328,372 | A | | 7/1994 | Reynaud et al. | |
| 5,332,390 | A | * | 7/1994 | Rosellini | 433/34 |
| 5,444,104 | A | | 8/1995 | Waknine | |
| 5,775,913 | A | * | 7/1998 | Updyke et al. | 433/223 |
| 5,839,900 | A | * | 11/1998 | Billet et al. | 433/218 |
| 5,947,737 | A | * | 9/1999 | Billet et al. | 433/223 |
| 5,964,592 | A | * | 10/1999 | Hites et al. | 433/221 |
| 6,010,337 | A | * | 1/2000 | Billet et al. | 433/218 |
| 6,267,597 | B1 | * | 7/2001 | Kim | 433/224 |

FOREIGN PATENT DOCUMENTS

| DE | 36 32 868 A1 | 10/1987 |
|---|---|---|
| DE | 87 14 974 U1 | 3/1988 |
| DE | 40 29 230 A1 | 3/1992 |
| DE | 43 34 608 A1 | 4/1995 |

* cited by examiner

*Primary Examiner*—James J. Seidleck
*Assistant Examiner*—Sanza L. McClendon
(74) *Attorney, Agent, or Firm*—John C. Thompson; Alan S. Korman

(57) ABSTRACT

Shaping cap made of ceramic, metal or plastic material, which is suitable as a solid constituent of dental pin structures.

4 Claims, 1 Drawing Sheet

SHAPING CAP FOR DENTAL PIN STRUCTURES

Figure 1:
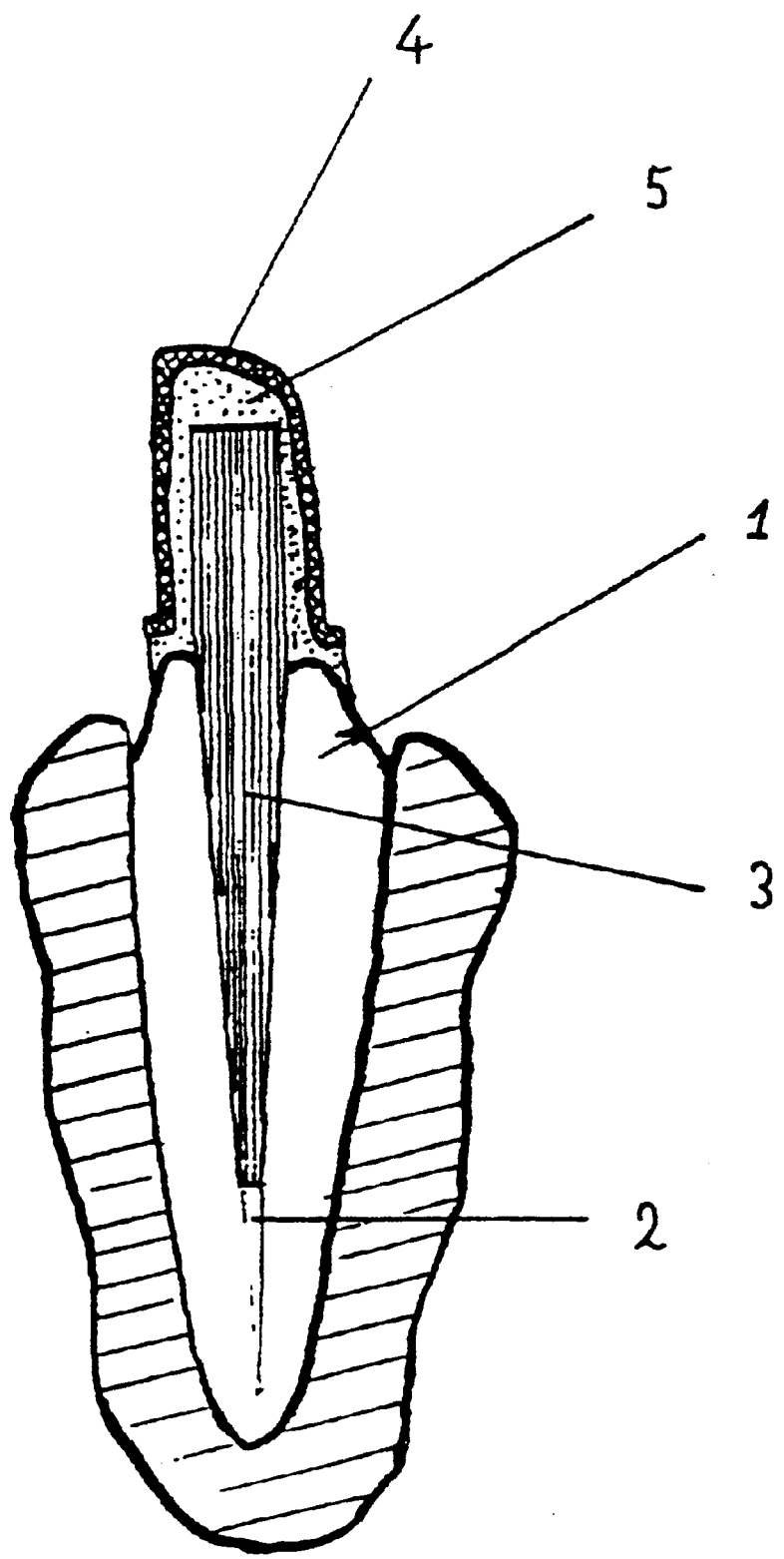

This application claims the benefit of Provisional application Ser. Nos. 60/263,371, filed Jan. 23, 2001, and 60/283,430, filed Apr. 12, 2001.

The invention relates to shaping caps for dental pin structures as well as kits and processes for the preparation of dental pin structures.

Anchorage pins are used to secure tooth restorations and to reconstruct missing hard tooth substance. These are usually inserted into the root canal and therefore also called root pins. However, besides the intracanalicular anchorage, a parapulpal anchorage is also usual.

The insertion of these pins into the root canal takes place in three phases. In the first phase, the root canal is prepared up to the apex with customary root canal instruments. In the second phase, the coronal part of the root is prepared with standardized drills. In the third phase, the anchorage or root pin is inserted into the prepared canal.

A so-called pin or stump structure is then modelled on the anchorage pin. The structures can be built up directly in the mouth of the patient with moldable materials such as amalgam and composite and be ground into the correct shape. However, they can also be prepared indirectly in the dental laboratory using an impression of the prepared hard tooth substance with the set pin. Lastly, this structure is crowned or veneered.

To manufacture pin structures from composite materials, caps of flexible plastic material such as silicone or polyethylene can be used as auxiliaries which allow easy shaping of a standard stump. The cap is usually filled with composite, pushed over the root pin and the composite is then cured. The caps consist of soft, flexible material and after curing can be easily removed from the cured composite material. The stump structure is then worked on further. The caps are obtainable for front and back teeth in different sizes. The composites used to prepare the structures contain, besides a polymerizable matrix material, usually particulate fillers. The load-bearing capacity of the structures is limited.

The object of the invention is to provide shaping caps for the preparation of dental pin structures with increased strength.

This object is achieved by shaping caps which are suitable as a permanent constituent of the pin structure.

The shaping caps consist of metal, preferably of ceramic or plastic material, those plastic materials being preferred which contain an organic matrix material and a filler, preferably fibrous filler.

Further preferred are tooth-coloured and in particular transparent shaping caps, so that the polymerizable material contained therein can be cured by light.

Particularly suited as matrix material are ionically and/or radically polymerizable mono- or multifunctional monomers, in particular mono(meth)acrylates such as methyl, ethyl, butyl, benzyl, furfuryl, or phenyl(meth)acrylate, multifunctional acrylates and methacrylates such as, for example, bisphenol (A) di(meth)acrylate, decanediol di(meth)acrylate, butanediol di(meth)acrylate, 1,10-decanediol di(meth)acrylate and/or 1,12-dodecanediol di(meth)acrylate.

Particularly preferred matrix materials are polycarbonate di(meth)acrylates, in particular the condensation product of a hydroxyalkyl methacrylate, preferably 2-hydroxyethyl methacrylate, and a bis(chloroformate), preferably triethylene glycolbis(chloroformate), polycarbonate tri- or tetra (meth)acrylates, urethane di-, tri-, tetra (meth)acrylates and mixtures of these. Monomers of this type are described in DE 36 32 868 A1 and U.S. Pat. No. 5,444,104.

Further particularly preferred monomers are bis-GMA (an addition product of methacrylic acid and bisphenol A-diglycidyl ether), UDMA (an addition product of 2-hydroxyethyl methacrylate and 2,2,4-hexamethylene diisocyanate), di-, tri-, (TEGDMA) and tetraethylene glycoldi(meth)acrylate, trimethylolpropane tri(meth)acrylate and pentaerythritol tetra(meth)acrylate.

To initiate the radical polymerization, the polymerizable component contains thermal and/or preferably photoinitiators.

Preferred initiators for the thermal curing are peroxides, such as for example dibenzoyl peroxide, dilauryl peroxide, tert.-butyl peroctoate and tert.-butyl perbenzoate as well as azobisisobutyro-ethylester, benzopinacol and 2,2-dimethylbenzopinacol.

Preferred photoinitiators are benzophenone and benzoin as well as their derivatives, á-diketones and their derivatives such as for example, 9,10 phenanthrenequinone, diacetyl and 4,4-dichlorobenzil. Particularly preferred photoinitiators are camphorquinone and 2,2 methoxy-2-phenyl-acetophenone and in particular combinations of á-diketones with amines as reduction agent, such as for example N-cyanoethyl-N-methylaniline, 4-(N,N-dimethylamino)-benzoic acid ester, N,N-dimethylaminoethyl methacrylate, N,N-dimethylsym.-xylidine or triethanolamine. In addition acylphosphines, such as for example 2,4,6-trimethylbenzoyldiphenyl- or bis-(2,6-dichlorobenzoyl)-4-N-propylphenyl phosphine oxide, are suitable as photoinitiators.

Diaryliodonium or triarylsulphonium-salts, such as for example triphenyl sulphonium-hexafluorophosphate and hexafluoroantimonate, are particularly suitable for the dual curing of radically and cationically polymerizable systems.

Redox initiator combinations, such as for example combinations of benzoyl or lauryl peroxide with N,N,-dimethyl-sym.-xylidine or N,N-dimethyl-p-toluidine, are used as initiators for a polymerization at room temperature. Further suitable initiators and accelerators are vitamin C and barbituric acid.

Besides polymerizable monomers and/or prepolymers, the matrix material also preferably contains fillers. Organic and inorganic fibrous materials, such as fibres, fibre mats and/or fabrics are preferred as fillers. Preferred are glass fibres, polyethylene fibres (Spectra, Dynema), polyamide, in particular aramid fibres (Kevlar), and carbon fibres, as well as mats and fabrics of these fibres.

The fibrous materials preferably have a fibre diameter of <0.25 mm, in particular 0.01 to 0.25 mm, and a ratio of fibre length to fibre diameter of >10:1, in particular >10:1 to 100:1.

So-called whiskers are also preferred as fibrous fillers. These are microfibres with a length of preferably 10 to 200 $\mu$m and a diameter of preferably 0.1 to 1 $\mu$m.

Alternatively or additionally to the fibrous fillers, the cap material can contain particulate fillers. Preferred particulate fillers are precipitated or ground plastics particles, preferably with a particle size of 0.02 to 100 $\mu$m; hybrid fillers such as ground polymerisate from an organic matrix with organic and/or inorganic fillers, the ground polymerisate preferably having a particle size of 0.5 to 80 $\mu$m; and/or inorganic fillers.

Particularly preferred particulate fillers are amorphous spherical materials on the basis of mixed oxides of $SiO_2$, $ZrO_2$ and/or $TiO_2$ (U.S. Ser. No. 08/025,810), microfine fillers such as pyrogenic silica or precipitate silica, spherical SiO$_2$ particles (precipitated particles) with a particle size of 200 to 700 nm as well as macro- (particles size of 5 μm to 200 μm) or mini-fillers (particle size of 0.5 to 5 μm), such as quartz, glass ceramic, or glass powders with an average particle size of 0.5 μm to 5 μm as well as X-ray opaque fillers such as ytterbium triflouride.

The organic and in particular the inorganic fillers are preferably provided with a suitable adhesion promoter, i.e. silanized for example, in order to guarantee a firm bond between fibre and matrix. Suitable silanes are known to the person skilled in the art. Preferred silanes are gamma-methacryloxypropyl-trimethoxy silane (A-174) and gamma-methacryloxypropyl-tris(2-methoxyethoxy) silane (A-175). These silanes are particularly suitable when the matrix material contains polymerizable (meth)acrylate groups.

Furthermore, the mixtures can contain further additives such as colouring agents (pigments and dyestuffs), stabilizers, aromatics, microbiocidal active ingredients, plasticizers and/or UV absorbers.

Particularly preferred cap materials are fibre-reinforced plastics on the basis of urethane dimethacrylate which are additionally reinforced with particulate inorganic filler, preferably glass powder, such as for example materials with the following composition:

| Component | Proportion (wt -%) |
| --- | --- |
| Urethane dimethacrylate | 10 to 20% |
| Glass fibres (silanized) | 60 to 70% |
| Glass powder (1 μm, silanized) | 15 to 20% |
| Pyrogenic silica (Aerosil) | 0.5 to 5% |
| Catalyst | 0.02 to 0.5% |

Further preferred cap materials are fabrics impregnated with organic binding agent such as for example:

| Component | Proportion (Wt -%) |
| --- | --- |
| Bis-GMA | 33 to 43%, e.g. 38% |
| Triethylene glycol dimethacrylate | 5 to 15%, e.g. 10% |
| Highly dispersed SiO$_2$ | 3 to 10%, e.g. 6% |
| Catalysts and stabilizers | 0.5 to 2%, e.g. 0.5% |
| Glass fibres (fabric, 8-ply) | 40 to 50%, e.g. 45.5% |

Furthermore, thermoplastics are preferred as cap materials, in particular those with a glass-transition temperature (Tg) of more than 40° C., preferably more than 80° C. and in particular more than 100° C. Particularly preferred are plastic materials with an elasticity modulus (E-modulus, measured according to EN ISO 178) of more than 2000 MPa (measured at room temperature), in particular more than 5000 MPa. Amongst the particularly preferred thermoplastics are polymethyl methacrylate (PMMA, Tg=105° C., E-modulus=3300 MPa), polysulphone (Tg=190° C., E-module=2700 MPa) and polycarbonate (TG=145° C., E-modulus=2300 MPa). Increasing the E-modulus of the plastic materials can be achieved by the addition of fillers, in particular fibrous fillers. For example, polysulphone, which is filled with 25 wt-% of glass fibres has an E-modulus of 7200 MPa. Consequently, thermoplastics which contain filler are preferred, in particular thermoplastics containing fibrous filler. The E-modulus can assume values of 25,000 MPa or even 50,000 MPa.

The matrix of the shaping caps can be in uncured, pre-cured or fully-cured form. It is essential that the caps maintain their shape. The use of a pre-cured, i.e. partially polymerized, material is preferred.

The surface, in particular the inner surface, of the shaping caps is provided with agents which guarantee a firm bond between cap and cap filling material. Caps of uncured or partially cured material contain polymerizable groups which ensure a firm bond between cap and cap filling material by chemical bonds after curing. When using a fully-cured material, as well as in the case of metal and ceramic caps, the surface of the caps is preferably modified in such a way that it contains polymerizable groups. Polymerizable groups can be applied to the cap surface, for example, by silanizing the caps. In the case of plastic caps it is advantageous if the plastic material contains inorganic filler, for example, glass powder or glass fibres, as silanizing agents react preferably with filler particles or filler fibres present on the cap surface. The above-named silanes are preferred as silanizing agents.

Preferred polymerizable groups are radically polymerizable groups, in particular ethylenically unsaturated groups such as vinyl, allyl, acryl, and methacryl groups.

To improve the adhesion between cap and cap filling material, the caps can also be treated with a solvent or a reactive thinner so that the cap material swells at its surface. This variant is particularly suited to fully-cured plastic caps.

Furthermore, firm adhesion can be achieved by mechanical means. For example, the cap surface can be roughened by sand-blasting to improve adhesion, or the surface can be provided with retentions such as undercuts, grooves or perforations.

Ceramic caps or caps from plastic materials which contain inorganic fillers, are preferably roughened and silanized to guarantee a firm bond between cap and cap filling material.

To improve adhesion, metal caps are preferably treated with phosphoric acid esters containing (meth)acrylate groups, such as e.g. the product Targis Link from the firm Ivoclar. The phosphoric acid groups of these esters react with the metal surface or metallic oxides present on the surface, accompanied by development of phosphate compounds, the (meth)acrylate groups are polymerizable and can react with the cap filling material. Furthermore, a thin, glass-like layer, a so-called SiO$_x$—C layer, can be applied to the metal surface, which can be silanized, e.g. with the silanes mentioned above. To this end, the metal surface is treated for example with the product Silocoater® from the firm Kulzer. Additionally, silicatic particles can be anchored to the metal surface by sand-blasting with a special blasting agent (Rocatac®, ESPE), these forming a thin ceramic layer which can also be silanized.

To prepare pin or stump structures, the caps are filled with a polymerizable material, preferably a polymerizable composite material (cap filling material) and fitted onto the prepared tooth or a model of it. Before filling, the cap can, optionally, be cut to size by scissors. The polymerizable material and, optionally, the cap is then cured, preferably by photopolymerization. The material is firmly bound to the cap.

Mixtures of the above-mentioned monomers, polymerization-initiators and preferably fillers also are particularly suited as cap-filling material, non-fibrous fillers being preferred as fillers. Preferred are materials which contain 20 to 80 wt-% of one or more polymerizable monomers, 20 to 80 wt-% filler and 0.05 to 2 wt-% polymerization initiator. The cap material preferably contains an initiator for the photopolymerization and can be cured by light. Particularly preferred cap-filling materials have the following compositions:

Fine-particle Hybrid

| Component | Proportion (wt-%) |
|---|---|
| Bis-GMA | 6 to 12%, e.g. 8.7% |
| Decanediol dimethacrylate | 3 to 7%, e.g. 4.7% |
| Urethane dimethacrylate | 6 to 14%, e.g. 9.0% |
| Barium glass filler (silanized) | 60 to 85%, e.g. 72.0% |
| Highly-dispersed $SiO_2$ | 3 to 7%, e.g. 5.0% |
| Catalysts and stabilizers | 0.2 to 1%, e.g. 0.6% |

Microfilled Composite

| Component | Proportion (wt-%) |
|---|---|
| Ethoxylated bisphenol A dimethacrylate | 36.0 to 68.0%, e.g. 53.2% |
| Triethylene glycol dimethacrylate | 11.0 to 17.0%, e.g. 13.3% |
| Antioxidants e.g. butylated hydroxytoluene | 0.002 to 0.02% 0.008% |
| Curing agent e.g. bornane-2,3-dione | 0.06 to 0.20% 0.12% |
| Curing accelerator e.g. ethyl-4-dimethylaminobenzoate | 0.05 to 0.20% 0.12% |
| Submicronic silanized $SiO_2$ | 15.0 to 55.0%, e.g. 33.3% |

Aerosil with a particle size of 0.01 to 0.04 μm and e.g. an average particle size of 0.02 μm is preferably used as submicronic $SiO_2$.

Macrofilled Composite

| Component | Proportion (wt-%) |
|---|---|
| Binding Agent | |
| Bis-GMA | 55 to 66%, e.g. 61.2% |
| Bisphenol A dimethacrylate | 5 to 9%, e.g. 6.8% |
| TEGDMA | 20 to 34%, e.g. 26.9% |
| Methacrylic acid | 1.5 to 2.5%, e.g. 2.0% |
| Benzil | 0.1 to 0.5%, e.g. 0.3% |
| Camphorquinone | 0.1 to 0.5%, e.g. 0.3% |
| 2-(N,N-dimethylamino) ethyl methacrylate | 2 to 3%, e.g. 2.5% |

The percentage data refer to the total mass of the binding agent.

20 to 35 wt-% of the binding agent is mixed with 65 to 80 wt-% silanized Ba—Al silicate glass as a filler to the ready to use composite, e.g. 28 wt-% of the binding agent and 72 wt-% of the filler.

In the course of the polymerization, the shaping caps are firmly bound to the polymerizable material and thus effect a distinct increase in the strength of the root-pin structure without the need for additional steps. Rather, the removal of the shaping caps used previously for shaping the pin structures no longer applies. The cap serves as the basic shape of the stump. This can, for example, be veneered or crowned later.

In contrast to previous shaping caps, the shaping caps form an integral part of the dental restoration, i.e. the caps remain permanently in the restoration and assume a supporting function there. The shaping caps consisting of soft, flexible plastic material which were used previously for the preparation of pin structures are unsuitable for this purpose as they possess insufficient mechanical strength. Additionally, these caps are so designed that they can be easily removed again after curing of the cap-filling material. The shaping caps according to the invention preferably have an E-modulus of at least 2000 MPa, particularly preferably 5000 MPa, in the cured state. Caps with an E-modulus of 10,000 MPa to 50,000 MPa and in particular of about 30,000 MPa (measured according to EN ISO 178 at room temperature, without cap-filling material) are quite particularly preferred.

The shaping caps are adapted in shape and size for use in dentistry. Caps which are matched to the shape and size of the tooth to be treated, such as incisor, canine tooth, premolar and molar are preferred. At their base, the caps preferably have an oval cross-section with a diameter in longitudinal direction of 6 to 11 mm and a diameter in transverse direction of 4 to 9 mm. The caps can for example have an elliptical cross-section with a ratio of large to small semiaxis of 1.22 to 1.68. The height of the caps is preferably 6 to 10 mm.

The shaping caps according to the invention effect a distinct increase in the strength of the whole root-pin structure and protect this from excessive stress peaks. The preparation of pin structures is additionally simplified as, on the one hand, the removal of the shaping cap is not required, while on the other hand, the use of standardized shaping caps simplifies matching e.g. of the crown.

Shaping cap and polymerizable material can be marketed separately or preferably together as a kit. According to a particularly preferred version, shaping caps filled with polymerizable material are marketed. The filling by the dentist or dental technician which was previously necessary is thus no longer required. Kits and shaping caps which contain polymerizable material are preferably marketed in packs which are impervious to oxygen and, where applicable, light, in order to prevent a premature curing of the material.

A further object of the invention are kits for the preparation of dental pin structures which contain at least one of the shaping caps described above, at least one anchorage pin and polymerizable material. The anchorage pins can be made of metal, ceramic, or preferably fibre-reinforced plastic. Furthermore, the kits can contain a material for the veneering of the shaping caps. The kits preferably contain a shaping cap on the basis of fibre-reinforced plastic material and are thus suitable in particular for the preparation of fibre-reinforced pin structures.

Alternatively, the kits can contain crowns or crown blanks which are preferably already matched to the size of the shaping cap.

To prepare a tooth restoration such as for example a crown, the tooth to be treated is first ground by the dentist and then, in the manner described above, fitted with an intracanicular or parapulpal anchorage pin. Then a suitable shaping cap is selected, the cap is filled if necessary with a polymerizable material, the filled shaping cap is fitted onto the anchorage pin and the polymerizable material is cured. This is thus firmly bound to the shaping cap and the anchorage pin. The construct consisting of anchorage pin, cap-filling material and shaping cap is called a pin or stump structure.

FIG. 1 shows a tooth root 1 with a root canal 2. A root pin 3 is inserted into the root canal 2. A fibre-reinforced shaping cap 4 which is filled with polymerizable material 5 is pushed over the root pin 3.

Either an impression of the thus-prepared tooth is then taken and a positive model for the manufacture of the crown in a dental laboratory is made or the tooth is treated further directly in the mouth of the patient. In the first case, the finished crown is secured to the prepared tooth with a fixing composite. In the second case, either a ready-made crown, matched to the shaping cap, is fitted onto the prepared tooth and ground or a crown is shaped through application of veneering material to the prepared tooth. Ready-made crowns are particularly suitable for temporary treatment of the tooth until the final crown is finished.

Two shaping caps, which are fitted onto the teeth bordering a tooth gap, can serve as the basis for a bridge.

The preparation of the dental restoration can also be carried out in a dental laboratory by a dental technician using a cast (ex vivo). For this purpose, an impression of the tooth is taken after insertion of the root pin and then a positive cast prepared of the tooth to be restored. This serves as a basis, for example, for the preparation of the stump structure or of the complete restoration consisting of stump structure and crown. The preparation of stump structure or dental restoration takes place in the manner described above. The stump construction or the complete restoration is then fitted to the patient by the dentist.

What is claimed is:

1. Shaping cap for dental pin structure, characterized in that shaping cap is suitable as a permanent constituent of the pin structure and consists of a material selected from the group consisting of ceramic, metal, plastic material and filler-containing plastic material, the cap having an E-modulus of at least 2000 MPa.

2. Kit for the preparation of tooth pin structures, said kit containing:
   an anchoring pin,
   a shaping cap suitable as a permanent constituent of the pin structure and consists of a material selected from the group consisting of ceramic, metal, plastic material and filler-containing plastic material, the cap having an E-modulus of at least 2000 MPa., and optionally polymerizable material.

3. Kit according to claim 2 characterized in that it additionally contains a material veneering the teeth.

4. Kit according to claim 2 characterized in that the anchoring pin consists of fibre-reinforced plastic.

* * * * *